(12) United States Patent
Cortes Ramirez et al.

(10) Patent No.: US 8,992,442 B2
(45) Date of Patent: Mar. 31, 2015

(54) BONE BIOPSY AND BONE MARROW ASPIRATION DEVICE

(75) Inventors: Jorge Armando Cortes Ramirez, Monterrey (MX); Sergio Gallegos Cazares, Monterrey (MX); Jose Rafael Borbolla Escoboza, Monterrey (MX); Lucio Florez Calderon, Guadalupe (MX); Manuel Ignacio Varela Jimenez, Monterrey (MX)

(73) Assignee: Instituto Tecnologico y de Estudios Superiores de Monterrey, Monterrey (MX)

( * ) Notice: Subject to any disclaimer, the term of this patent is extended or adjusted under 35 U.S.C. 154(b) by 1031 days.

(21) Appl. No.: 12/676,808

(22) PCT Filed: Sep. 5, 2008

(86) PCT No.: PCT/MX2008/000121
§ 371 (c)(1),
(2), (4) Date: Mar. 5, 2010

(87) PCT Pub. No.: WO2009/031880
PCT Pub. Date: Mar. 12, 2009

(65) Prior Publication Data
US 2010/0234761 A1    Sep. 16, 2010

(30) Foreign Application Priority Data
Sep. 7, 2007    (MX) .................... MX/a/2007/010963

(51) Int. Cl.
*A61B 10/00*    (2006.01)
*A61B 10/02*    (2006.01)
(52) U.S. Cl.
CPC ....... *A61B 10/025* (2013.01); *A61B 2010/0258* (2013.01)

USPC ........... 600/567; 600/562; 600/563; 600/564; 600/565; 600/566; 604/19

(58) Field of Classification Search
USPC .................... 600/562–572; 604/174; 424/423
See application file for complete search history.

(56) References Cited

U.S. PATENT DOCUMENTS

| 4,513,754 | A |   | 4/1985  | Lee |
| 4,793,363 | A |   | 12/1988 | Ausherman et al. |
| 5,257,632 | A |   | 11/1993 | Turkel et al. |
| 5,357,974 | A | * | 10/1994 | Baldridge ..................... 600/567 |
| 5,522,398 | A |   | 6/1996  | Goldenberg et al. |
| 5,807,275 | A |   | 9/1998  | Jamshidi |
| 6,015,391 | A | * | 1/2000  | Rishton et al. ................ 600/567 |

(Continued)

*Primary Examiner* — Rene Towa
(74) *Attorney, Agent, or Firm* — Baker & McKenzie LLP

(57) ABSTRACT

The invention relates to a device for taking a liquid bone marrow sample (aspiration) and a solid bone sample (biopsy) in the same procedure, which can thus replace specialized needles for taking bone marrow and needles exclusively used for taking bone biopsies. The device for taking liquid bone marrow samples and a solid bone sample has a simple mechanism that uses two grooved clamps, it is easy to disassemble for sterilization and its handle is designed to perform the puncture easily. The needle of the device is hollow, and within it a guide is placed with two sections of different diameters. The guide makes it possible to open up the empty needle channel to allow the bone marrow liquid to flow and be extracted, and also to close the channel to be able to penetrate the tissue. The purpose of this invention is to combine the procedures of bone marrow aspiration and bone biopsy, thus reducing the patient's discomfort and the time needed for the procedure.

20 Claims, 8 Drawing Sheets

(56) References Cited

U.S. PATENT DOCUMENTS

| | | |
|---|---|---|
| 6,221,029 B1 | 4/2001 | Mathis et al. |
| 2003/0139688 A1 | 7/2003 | Lamoureux |
| 2007/0142744 A1* | 6/2007 | Provencher .................. 600/562 |
| 2007/0198013 A1* | 8/2007 | Foley et al. ..................... 606/57 |

* cited by examiner

BONE BIOPSY AND BONE MARROW ASPIRATION DEVICE

TECHNICAL FIELD OF THE INVENTION

The invention relates to a device for taking a liquid bone marrow sample (aspiration) and a solid bone sample (biopsy) in the same procedure, which uses a needle, a guide, a handle and a mechanism for the movement of the guide. With this invention we intend to avoid using one needle to aspirate the bone marrow and then using another needle to perform the bone biopsy, thus avoiding penetrating the patient twice and changing the equipment for the procedure.

BACKGROUND

Currently, the conventional procedure for bone marrow aspiration and bone biopsy is conducted separately, in a manner that uses specialized needles exclusively for bone marrow liquid aspiration and needles exclusively for performing the bone biopsy. The instruments used for these procedures have the same mechanical structure, their difference lies in the dimensions: the bone needle biopsy needle is much longer and has a larger diameter, while the marrow needle is thinner and has a bevel with a greater pitch.

Some similar devices are:

The Coaxial Bone Marrow Biopsy Coring and Aspirating Needle Assembly and Method of Use Thereof (U.S. Pat. No. 5,257,632) (1993) describes an invention which obtains a solid sample of bone marrow and a liquid sample of bone marrow by aspiration. It consists of an aspiration assembly which surrounds the interior orifice of the needle and a trocar which extends around the needle. It has a handle which allows the insertion of the stylet, the needle and the assembly, one within the other, into the bone, which enables manipulation. After the insertion of the combined system, the trocar is withdrawn. By pushing and turning, a piece of bone is inserted into the needle. Then, the needle is withdrawn and the bone marrow sample is pushed out. An aspiration system is then attached to an aspiration channel attached to the handle of the exterior sheath, and the liquid bone marrow sample is taken. The device presented in this document is simpler, the needle is inserted with the guide into the patient, when the bone is reached, the needle is raised and the aspiration is performed, without having to withdraw it and is then inserted more deeply in order for the needle to penetrate into the bone and the biopsy is successfully performed.

More recent patents are the patent submitted in the document Bone marrow biopsy needle (U.S. Pat. No. 5,522,398) (1997) which has the trade name Snarecoil. The invention consists of an exterior cannula, an internal tube, and a guide. The far end of the interior tube is provided with a trap in the form of a coil extending from the interior tube. The free side of the interior tube is adhered to the internal surface of the exterior cannula. To the extent that there is rotation of the interior tube with respect to the exterior cannula, the coil will decrease in diameter to take the piece of the biopsy with the exterior needle. After the removal of the needle from the patient, rotating the interior tube in the opposite direction will cause the tube to expand to its original diameter and will allow removal of the piece of the biopsy from the needle.

SUMMARY

The tool that is the subject of this invention is a needle with special characteristics capable of performing separate procedures of puncturing and aspiration of bone marrow and bone in a single procedure in a simpler manner which is less painful for the patient, so that in a two-in-one procedure, bone marrow and a solid sample of bone are extracted. Also, in the invention presented in this document, there is no trap-type system to take the biopsy before extracting it as in some conventional tools, and the movable element is not used to take the sample, but rather, to retract the needle.

Unlike previous devices, the present invention has a very simple mechanism based on a needle and a guide, in addition, the mechanism that it uses has only two steps, and it is easy to dismantle for sterilization. The handle is designed so that it will be easier to hold and apply force, making it possible to obtain good results with less force. A principal advantage is the simplicity of the entire device and its operation, which makes the procedure easier for the user and in a single puncture, takes the liquid sample of the bone marrow and a solid bone sample; both samples taken in optimal conditions for laboratory analysis.

The single two-step procedure begins with the insertion of a special needle for the procedure in the posterior portion of the iliac crest. After passing through skin, fat, and bone, one arrives at the marrow, where the guide is raised in order to begin to take the required sample as quickly as possible (because this substance coagulates, becoming thicker and making it impossible to take the sample). Once again the guide is lowered in order to continue inserting the needle until it reaches the bone, when it reaches the bone, the guide is lifted again to take the bone biopsy. After the sample is taken, the needle is withdrawn from the patient and with the help of the guide, the sample taken is expelled.

DETAILED DESCRIPTION OF THE INVENTION

The invention consists of a device for bone marrow aspiration and bone biopsy capable of performing in a single procedure the taking of a liquid bone marrow sample and a solid bone sample, with no need to puncture the patient with a special needle to take the liquid sample (aspiration), to withdraw it, and then to insert another special needle to take the solid bone (biopsy). The objective is to reduce trauma to the patient and to avoid the double work for the doctor who performs the procedures.

For greater comprehension since it is described in this technical memorandum, we rely on the figures in which the device, its components, and the positions that make it possible to adopt its use are represented.

Figure 1:
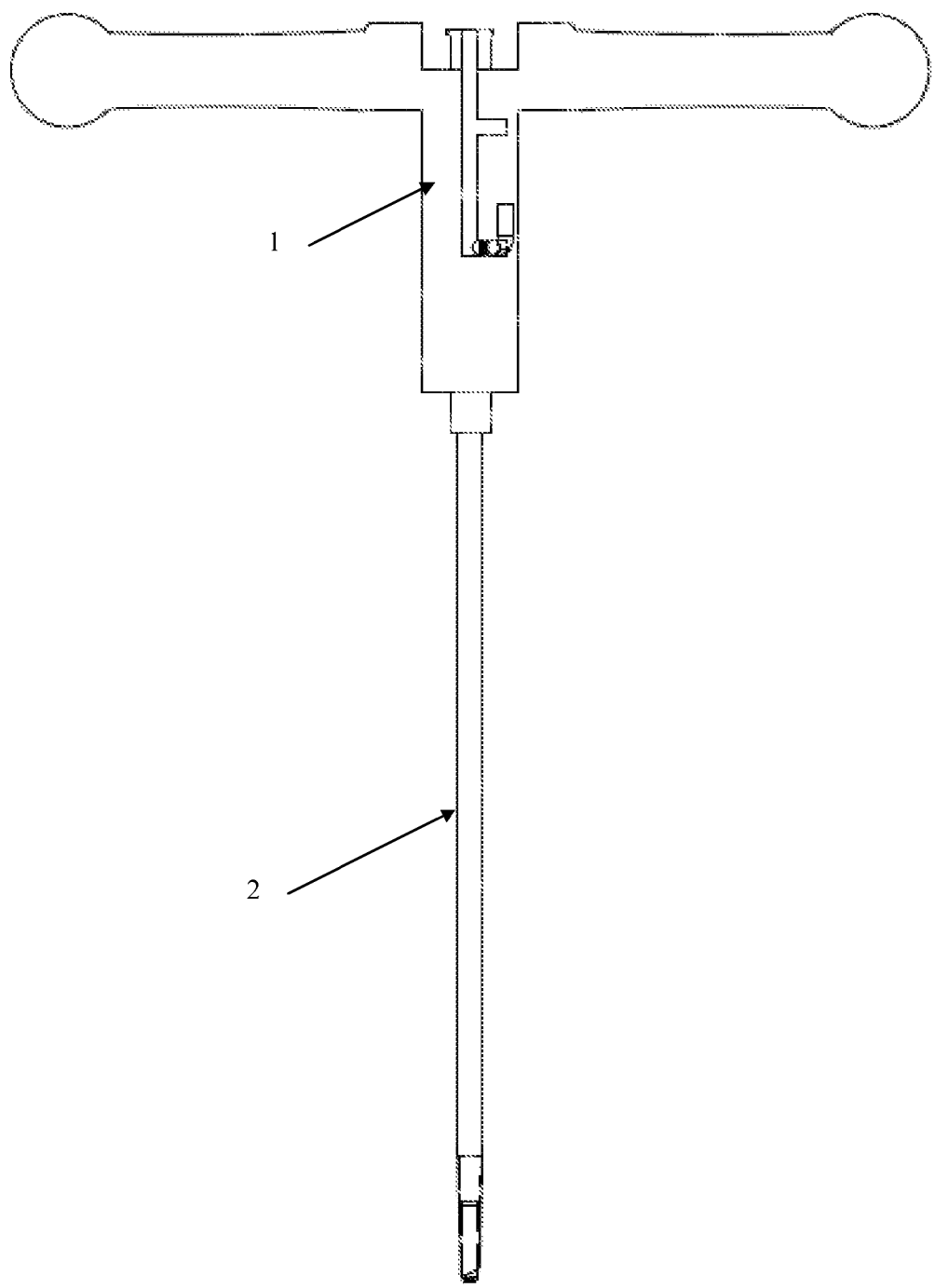
FIG. 1: Frontal view of the Bone Biopsy and Bone Marrow Aspiration Device

In FIG. 1, the frontal view of the Device is represented for bone marrow aspiration and bone biopsy, in which the principal elements which form the Device, a handle (1) which has a "T" shape and a puncturing device (2) are shown.

Figure 2:
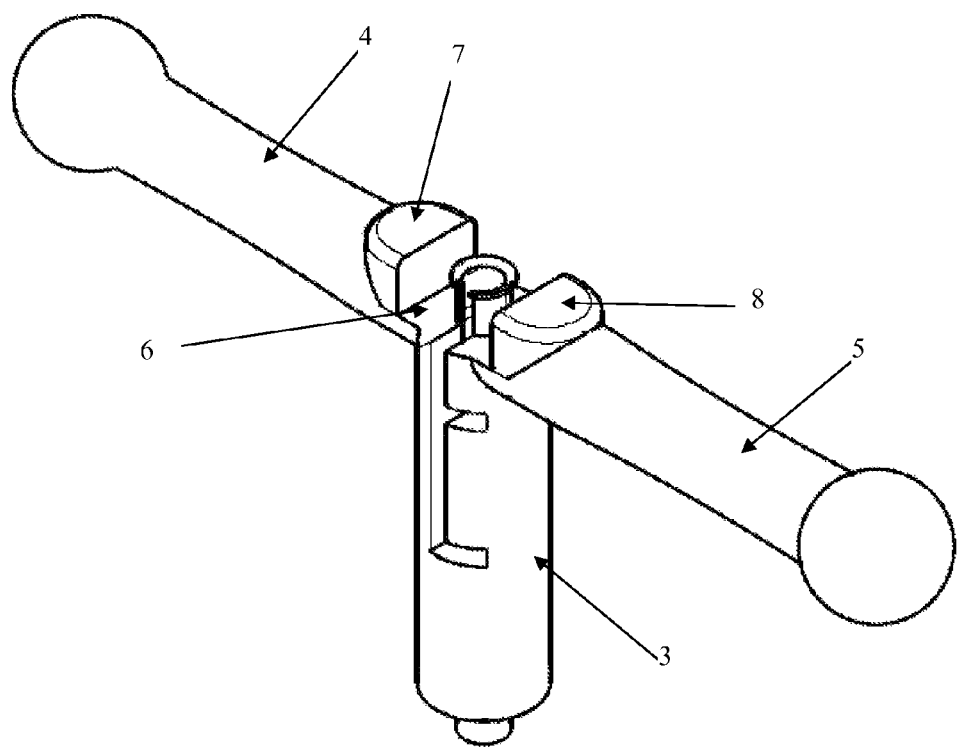
FIG. 2: Isometric view of the handle

FIG. 2 illustrates an isometric view of the handle; and identifies the elements of the handle (1) which consists of a main cylinder (3) in the upper part of which two lateral supports are extended (4 and 5) which are slightly convex and which have a spherical end, in the upper part of the part of the main cylinder (3) a quadrangular "pull" (6) is located which has upper surfaces (7 and 8) located on the sides of the pull which are flat, in a horizontal position in order to serve as a support for the palm of the user's hand and the user can manipulate and insert the device forcefully and easily into the patient.

Figure 3:
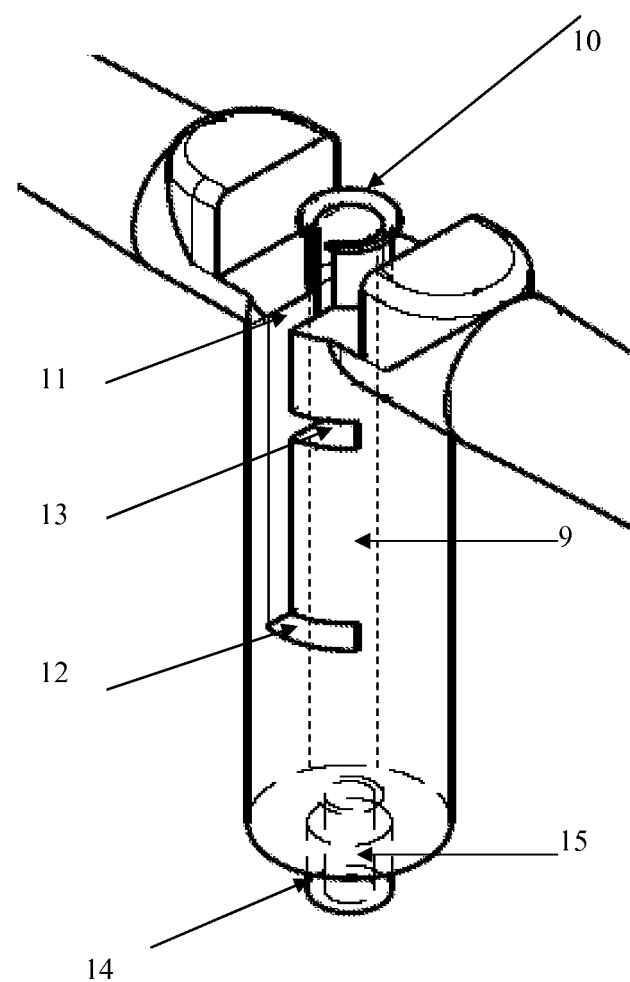
FIG. 3: Isometric view with hidden lines of the handle

FIG. 3 shows an isometric view with hidden lines of the main cylinder (3) has a central perforation (9) which crosses through them longitudinally; by the upper part of the central perforation (9) a cylindrical peripheral wall (10) is located which extends up but does not reach the upper level of the lateral supports (4 and 5), thus having a connection (10) for a "Luer Lock" type syringe which has a standard size, shape, and geometry for the connection of syringes of different capacities depending on the user's requirements, this cylindrical peripheral wall (10) is discontinuous, thus having a vertical groove (11) which extends up to the middle of the length of the main cylinder (3) and up to the central perforation (9). In addition, first and second horizontal grooves are shown, both make a cut of 40 degrees around the main cylinder (3) (if the measurement of the horizontal grooves was linear, they would be approximately 4.5 cm), the first horizontal groove (12) begins at the lower end of the vertical groove extending up to the central perforation (9) of the main cylinder (3), and the second horizontal groove (13) begins in the middle part of the vertical groove (11) extending up to the larger central perforation (9) of the main cylinder (3). Both horizontal grooves have a length of approximately 4.5 cm. In the lower part of the main cylinder (see FIG. 3), a holder (14) of the puncturing device (2) is located. The holder (14) has a length of 5 millimeters and has a smaller diameter than the larger central perforation (9) of the main cylinder (3), thus having a rung. The puncturing device (2) which consists of a needle and which is joined to the handle 1) is inserted with pressure into the smaller central perforation (15) of the holder (14).

Figure 4:
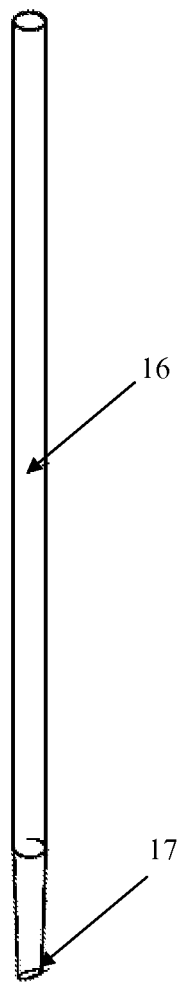
FIG. 4: Isometric view of the needle
Figure 5:
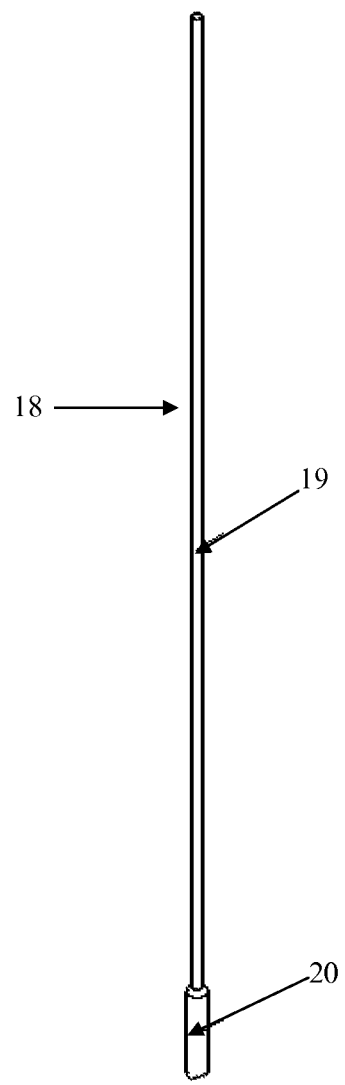
FIG. 5: Isometric view of the guide
Figure 6:
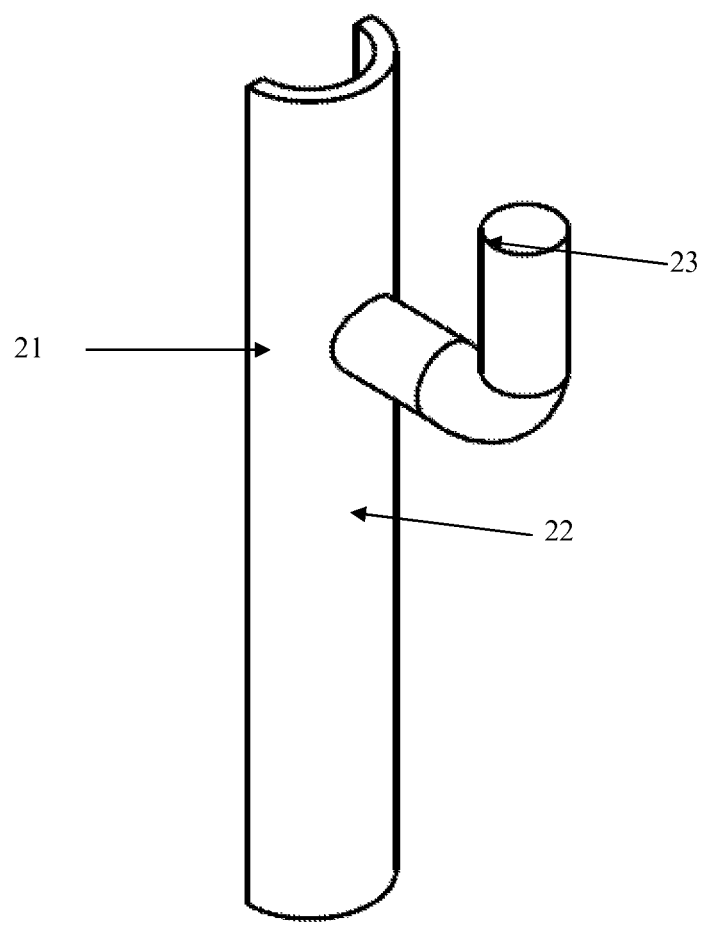
FIG. 6: Isometric view of the lever cover
Figure 7:
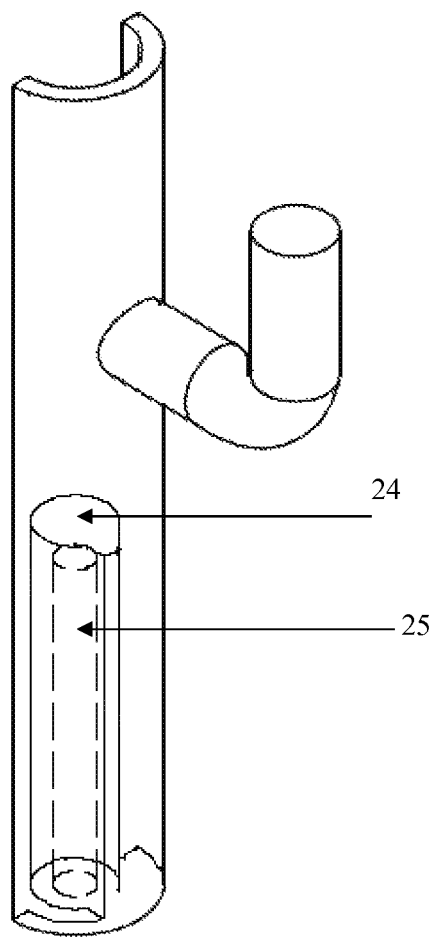
FIG. 7: Isometric view with hidden lines of the lever cover

FIG. 4 shows an isometric view of the needle (16) which is hollow and has a beveled edge (17) with a sloped angle of approximately 25 degrees which facilitates penetration into the tissue and bone of the patient. A guide (18) is located in the interior of the needle (16), which as observed in FIG. 5, is a single piece, which consists of a one-piece bar of 12 to 20 cm in length, preferably 15 cm, which has a first section (19) which has a first diameter and a second section (20) at the lower end, which has a second diameter, which has rungs, the first section being of greater length than the second section and, the diameter of the first section is less than the diameter of the second section. The total length of the guide is longer than the length of the needle. The guide (18) is held by its upper end to a lever cover (21), illustrated in an isometric view in FIG. 6, the lever cover (21) consists of a single piece, and consists of a semicircular plate (22) with a radius of 2 millimeters, by the external part of the semicircular plate, at three-quarters of its length is located an L-shaped lever (23). This lever is at a higher position than the vertical cylinder (24) located in the internal portion of the lever cover (21). This vertical cylinder (24) can be seen in FIG. 7 which shows an isometric view of the lever cover with cross-sections. This vertical cylinder (24) begins in the middle of the semicircular plate (22) and ends in the lower part. The vertical cylinder (24) has a central perforation (25) which does not pass through its entire length, to which the guide is connected (by the upper part of the second section).

As a result of the different diameter of the guide, it can be displaced by the horizontal and vertical grooves on the lever cover for the purpose of joining or separating the second section of the guide with the beveled edge of the needle, thus enabling the opening and closing of a channel.

The lever cover adjusts the position of the guide, and closes the vertical groove and the first and second horizontal grooves so that it is possible to create the required vacuum when the marrow aspiration is performed.

The lever cover (21) has a two-fold objective: the first allows manipulation of the position of the guide (18), and the second allows the vertical groove (11) of the peripheral cylindrical wall and the horizontal grooves (12 and 13) to be closed in order to enable the required vacuum to be created when the bone marrow aspiration is performed.

Preferred Device Assembly

The device which is the subject of this invention can be dismantled for sterilization. Assembly is completed in the following steps:
  a) Insert the lever cover (21) into the central perforation (9) of the main cylinder (11) sliding the lever (23) through the vertical groove (11) to the bottom, and then slide the lever (23) in the direction of the first horizontal groove (12) to the bottom of that horizontal groove.
  b) Insert the upper end of the first section of the guide (19) into the central perforation (9) of the vertical cylinder (11) of the lever cover (21).
  c) Insert the guide (19) into the needle (2) and insert that needle into the holder (14).

Preferred Method of Manipulation

Insert the closed bone marrow aspiration and bone biopsy device into the patient. In other words, the lever (23) must be at the bottom of the first horizontal groove (12) of the main cylinder, thus enabling the second section (20) of the guide (18) to meet the bevel (17) of the needle, and due to the difference in the diameter of the needle and the guide, a channel is formed (26) and is closed, to illustrate, what is described here can be observed in FIG. 8, with a frontal view of the device with hidden views.

Figure 8:
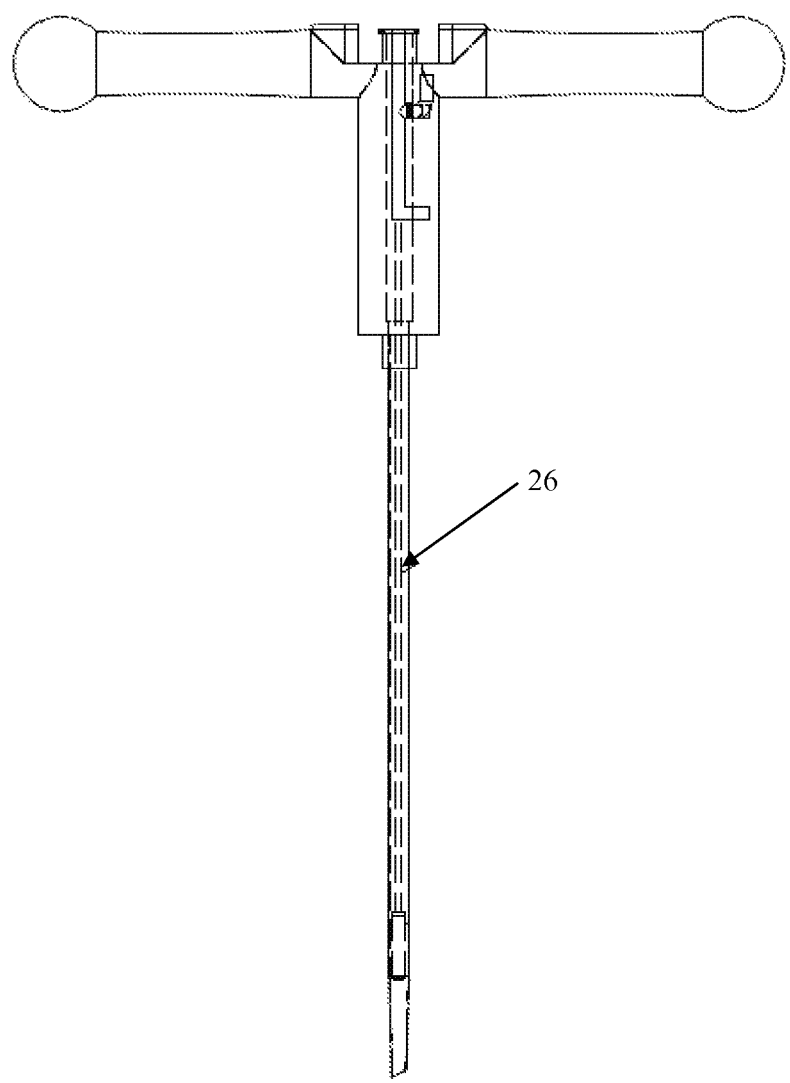
FIG. 8: Frontal view of the device with the open channel

The needle (2) is inserted into the patient until it reaches the marrow area, and then the device is opened, remaining as shown in FIG. 8. This consists of rotating the lever (23) around the first horizontal groove (12) until it touches the vertical groove (11), then sliding it vertically up over the vertical groove, until it is raised to the height of the second horizontal groove (13) and is rotated in order to insert the lever into that groove until it is joined.

As the guide (18) is joined to the lever cover (21); with the previous movement, the guide (18) has been lifted and the lever cover (21) has closed the vertical groove (11) and the vertical grooves (12 and 13), leaving the channel (26) open, as shown in FIG. 8, in order to then place a syringe into the connection (10).

Only the syringe is connected, the orifice of its lower end remains inside of the connection (10) so that lifting the plunger of the syringe causes a vacuum effect inside of the channel (26) which causes the bone marrow liquid to be introduced into the channel and to flow toward the syringe, thus completing the aspiration procedure. Subsequently, the device is closed and the syringe is removed.

The device is inserted deeper into the patient, hard bone is reached and when this occurs, the lever is manipulated (23) to open the device as shown in FIG. 8, and the device is inserted deeper into the patient until the bone penetrates into the interior of the channel (26). After this has occurred, the device is moved from side to side to fracture the bone and, finally, to withdraw it from the patient. As the last step, the device is extracted from the patient.

In order to extract the bone sample from the device, the device is closed, causing the guide (18) to make contact with the piece of bone and it pushes it until it is expelled from the needle (2).

Having sufficiently described my invention, I consider that which is contained in the following clauses to be new and, therefore, claim as my exclusive property:

1. A device for bone marrow aspiration and bone biopsy, the device comprising:
    a T-shaped handle and a puncturing device, where the T-shaped handle is comprised of a main cylinder from a proximal end of the handle, of which are extended two slightly convex lateral supports, and a pull is located at a proximal portion of the main cylinder;
    wherein the main cylinder has a central perforation that passes entirely through the main cylinder longitudinally, wherein in a proximal portion of the central perforation is located a peripheral cylindrical wall which extends upward without reaching a proximal level of the lateral supports, wherein the peripheral cylindrical wall is discontinuous, making a vertical groove which extends up to the middle of the length of the main cylinder and up to the central perforation,
    wherein around the main cylinder are first and second horizontal grooves comprising:
        the first horizontal groove beginning at the distal end of the vertical groove and extending horizontally partially around the main cylinder, and
        the second horizontal groove beginning in a middle part of the vertical groove and extending horizontally partially around the main cylinder, and
    wherein in a distal portion of the main cylinder is located a gripping means for the puncturing device and has a central perforation concentric with the central perforation of the main cylinder, the perforation of the gripping means having a smaller diameter than the perforation of the main cylinder, thereby forming a rung;
    wherein the puncturing device consists of comprises a hollow needle with a beveled distal end, the interior of which contains a guide which is longer than the puncturing device needle, wherein the guide:
        comprises a bar that has a first section which has one diameter and a second section at a distal end which has a second diameter, and thereby has rungs because the first section is longer than the second section,
        wherein the diameter of the first section is smaller than the diameter of the second section, wherein the second section makes contact with the interior of the beveled end of the puncturing device, and
    wherein a lever cover is located inside of the central perforation of the main cylinder of the handle, and is comprised of a semicircular plate, a concave part of the lever cover having a vertical cylinder which begins from a proximal portion of the semicircular plate and ends at a distal portion of the semicircular plate,
    wherein the vertical cylinder has a central perforation, which does not pass entirely through its length,
    wherein the lever covers further comprises a lever located on a convex part along the length of the plate and operable to be disposed within the vertical and first and second grooves of the main cylinder,
    wherein the lever is at a higher position than the vertical cylinder, and
    wherein a proximal portion of the guide is connected to the central perforation of the vertical cylinder of the lever cover such that when the lever is disposed along the vertical and first and second grooves the guide can be joined or separated from the beveled end of the hollow needle.

2. The device for bone marrow aspiration and bone biopsy according to claim 1, wherein proximal surfaces of the handle are located on sides of the pull, are flat, are in a horizontal position, and serve as a support for the palm of a user's hand to facilitate manipulation of the device for bone marrow aspiration and bone biopsy.

3. The bone marrow aspiration and bone biopsy device according to claim 1, wherein the horizontal grooves in the handle extend in the same direction.

4. The bone marrow aspiration and bone biopsy device according to claim 1, wherein the puncturing device is hollow with an internal diameter of 2 to 5 millimeters, has a length of 10 to 15 centimeters, and a distal end of the puncturing device has the bevel with a pitch of approximately 25 degrees.

5. The bone marrow aspiration and bone biopsy device according to claim 4, wherein the puncturing device has an internal diameter of about 3 millimeters and has a length of about 11 centimeters.

6. The bone marrow aspiration and bone biopsy device according to claim 1, wherein the puncturing device has an internal diameter that allows the guide to be moved inside of the puncturing device in order to open and close the opening at the distal beveled end of the needle.

7. The bone marrow aspiration and bone biopsy device according to claim 1, wherein the guide is slightly longer than the needle, and measures between 12 and 20 centimeters.

8. The bone marrow aspiration and bone biopsy device according to claim 7, wherein the length of the guide is about 15 centimeters.

9. The bone marrow aspiration and bone biopsy device according to claim 1, wherein the guide is designed with variation in the diameter, so that a channel is formed inside of the puncturing device through which the bone marrow liquid flows when the guide is moved upwards vertically.

10. The bone marrow aspiration and bone biopsy device according to claim 1, the lever cover is located inside of the central perforation of the main cylinder and the lever cover's length is equal to the sum of the length of the vertical groove and the length of the groove in the peripheral wall which extends to the proximal part of the main cylinder.

11. The bone marrow aspiration and bone biopsy device according to claim 1, wherein the lever is the element moved through the vertical groove and the first and second horizontal grooves, and, the lever is operable to control the position of the guide to open or close a channel formed with the needle.

12. The bone marrow aspiration and bone biopsy device according to claim 1, the lever cover adjusts the position of the guide, and is rotated to close the vertical groove in addition to the horizontal grooves to thus enable the necessary vacuum to be created when the bone marrow aspiration is performed.

13. The bone marrow aspiration and bone biopsy device according to claim 1, wherein the first and second horizontal grooves each have a radial cut of about 40 degrees around the main cylinder.

14. The bone marrow aspiration and bone biopsy device according to claim 1, wherein the gripping means has a length of about 5 cm.

15. The bone marrow aspiration and bone biopsy device according to claim 1, wherein the semicircular plate comprises about a 2 millimeter radius.

16. A method for assembling the bone marrow aspiration and bone biopsy device defined in claim 1, the method comprising:
   a) inserting the lever cover into the central perforation of the main cylinder, sliding the lever through the vertical groove of the main cylinder to the bottom of the vertical groove and then sliding the lever in the direction of the first horizontal groove to the end of that horizontal groove;
   b) inserting the proximal end of the first section of the guide into the central perforation of the vertical cylinder of the lever cover; and
   c) introducing the guide into the puncturing device and inserting that puncturing device into the gripping means for the puncturing device.

17. The method for assembly of the bone marrow aspiration and bone biopsy device according to claim 16, wherein when the position of the lever on the horizontal grooves is changed, the channel formed by the guide and the needle is opened and closed.

18. A method of manipulation for a bone marrow aspiration and bone biopsy device as recited in claim 1, the method comprising:
   a) closing the bone marrow aspiration and bone biopsy device by pushing the second section of the guide against an interior surface of the beveled end of the puncturing device;
   b) inserting the closed beveled end into a bone until it reaches a marrow area;
   c) opening the device by rotating the lever about the first horizontal groove on the main cylinder of the handle, and pulling the second section of the guide away from the interior surface of the beveled end of the puncturing device;
   d) lifting a plunger of a syringe connected to the device by displacing the lever along the vertical groove on the main cylinder of the handle to cause a vacuum effect inside of a channel defined between the puncturing device and the guide that aspirates bone marrow liquid toward the syringe and inside the channel with the vacuum effect;
   e) inserting the puncturing device deeper into the bone until hard bone is reached;
   f) opening the device by rotating the lever about the second horizontal groove the main cylinder of the handle, and pulling the second section of the guide away from the interior surface of the beveled end of the puncturing device;
   g) inserting the device into hard bone until a portion of hard bone enters into the channel;
   h) fracturing said portion of hard bone with movement of the device;
   i) removing the device from the bone.

19. A method of manipulation for a bone marrow aspiration and bone biopsy device as recited in claim 18, wherein lifting the plunger of the syringe to aspirate bone marrow liquid toward the syringe further comprises receiving liquid bone marrow into the syringe.

20. A method of manipulation for a bone marrow aspiration and bone biopsy device as recited in claim 18, the method further comprising extracting the portion of hard bone from the device by pushing the second section of the guide towards the beveled end so the second section of the guide makes contact with the portion of hard bone and pushes out of the beveled end of the puncturing device.

* * * * *

UNITED STATES PATENT AND TRADEMARK OFFICE
CERTIFICATE OF CORRECTION

PATENT NO. : 8,992,442 B2  Page 1 of 1
APPLICATION NO. : 12/676808
DATED : March 31, 2015
INVENTOR(S) : Jorge Armando Cortes Ramirez et al.

It is certified that error appears in the above-identified patent and that said Letters Patent is hereby corrected as shown below:

In the claims

Column 5, Claim 1, Line 42, after "device" delete "consists of".

Signed and Sealed this
First Day of March, 2016

Michelle K. Lee
*Director of the United States Patent and Trademark Office*